(12) United States Patent
La Fontaine

(10) Patent No.: US 9,707,384 B2
(45) Date of Patent: Jul. 18, 2017

(54) NEEDLE MODULE AND DEVICE FOR PIERCING THE SKIN

(71) Applicants: Rene La Fontaine, Herxheim (DE); Holger Hoffmann, Hamburg (DE)

(72) Inventor: Helmut La Fontaine, Marbella (ES)

(73) Assignees: Rene La Fontaine, Herxheim (DE); Holger Hoffmann, Hamburg (DE)

( * ) Notice: Subject to any disclaimer, the term of this patent is extended or adjusted under 35 U.S.C. 154(b) by 341 days.

(21) Appl. No.: 14/332,651

(22) Filed: Jul. 16, 2014

(65) Prior Publication Data

US 2015/0025561 A1    Jan. 22, 2015

(30) Foreign Application Priority Data

Jul. 16, 2013   (EP) .................................... 13003581

(51) Int. Cl.
*A61M 37/00*   (2006.01)

(52) U.S. Cl.
CPC ... *A61M 37/0076* (2013.01); *A61M 2205/106* (2013.01); *A61M 2205/8206* (2013.01)

(58) Field of Classification Search
CPC ...... A61M 37/0076; A61M 2205/8206; A61M 2205/106
USPC .................................................. 606/185, 186
See application file for complete search history.

(56) References Cited

U.S. PATENT DOCUMENTS

| | | | | |
|---|---|---|---|---|
| 5,471,102 A | * | 11/1995 | Becker | A61M 37/0076 310/17 |
| 6,345,553 B1 | | 2/2002 | Adler et al. | |
| 7,380,480 B1 | * | 6/2008 | Chen | A61M 37/0076 604/198 |
| 2003/0195542 A1 | * | 10/2003 | Lee | A61M 37/0076 606/186 |

FOREIGN PATENT DOCUMENTS

| | | |
|---|---|---|
| DE | 103 43 590 A1 | 4/2005 |
| EP | 1 743 673 A1 | 1/2007 |
| EP | 1 872 823 A1 | 1/2008 |
| EP | 2 420 265 A2 | 2/2012 |

OTHER PUBLICATIONS

European Search Report, Application No. EP 13003581.9, Apr. 16, 2014, 11 pgs.

* cited by examiner

*Primary Examiner* — Vy Bui
(74) *Attorney, Agent, or Firm* — Paul D. Strain, Esq.; Strain & Strain PLLC

(57) ABSTRACT

The present invention relates to a needle module, which comprises a piercing means on a mounting, which can be releasably coupled to the drive unit so that, as a result of a driving force exerted by the drive unit on the mounting, a repeated pushing movement moving the piercing means in and out is transmitted, wherein, according to the invention, the mounting has a safety device which mechanically irreversibly blocks the piercing means after the needle module has been released from the drive unit so that it can no longer (Continued)

be moved out of the needle module. The invention also relates to a device, in particular a hand device, for piercing the skin, comprising a drive unit and the needle module according to the invention.

28 Claims, 7 Drawing Sheets

Magnet and ferromagnetic material

Socket and ball

Velcro fastener a   b   c   d a b c

NEEDLE MODULE AND DEVICE FOR PIERCING THE SKIN

The present invention relates to a needle module which can be coupled to a drive device to form a device for piercing the skin, e.g. for permanent make-up or tattooing.

When pigmenting the skin, which can be divided into tattooing and permanent make-up, numerous specific colour pigments are inserted or transported into the layers of the skin organ by piercing the skin using a specially shaped needle or a needle system consisting of a number of needles. Agents can also be introduced into the skin using similar devices in medicine.

A typical hand device for piercing the skin consists of a drive unit and a needle module releasably connected to it. The drive unit usually comprises a motor, a gear unit and a drive to generate an oscillating back-and-forth movement of the needle. The needle module comprises the needle or the needle system which is accommodated in a needle holder. The needle holder can be connected to the drive unit. For this purpose, the drive unit usually contains a push rod with a special slot into which the needle holder, depending on the manufacturer, is pushed, inserted and/or clamped.

The needle may be a specifically shaped, individual needle or a needle system, i.e. a combination of a number of needles. During piercing, the needle carries out an oscillating back-and-forth movement at a speed and insertion depth which can be set by the operator. The insertion process is therefore carried out in a defined manner. The aim is to introduce a predefined dye (or agent) into lower lying layers of the skin through oscillating piercing. The needle is either regularly dipped into the dye or agent or the dye or agent is arranged in a reservoir in the needle module.

At the start of treatment, a (usually sterile) needle is connected to the drive unit of the device. At the end of treatment, the needle with the needle guide should be disposed of.

Such devices, in particular hand devices, for piercing the skin are known per se and are described, for example, in EP 1 743 673 A1 and EP 1 872 823 A1.

According to EP 1 743 673 A1, the resisting force when piercing should be measured and, via a control device connected to the hand device, a change in the resisting force should be reacted to by a change in the repeating frequency of insertion.

EP 1 872 823 A1 proposes providing, on the needle module, an identification unit which is evaluated by an evaluation device on the drive unit. This should, in particular, prevent the coupling of a needle module which is incompatible with the drive unit. However, information on permissible operating parameters of the needle module can also be provided and evaluated. In addition, the identification unit in the form of an electronic data memory, e.g. an RFID chip, makes it possible to block impermissible multiple use of a needle module. Such a safety device is highly desirable, but an electronic identification unit requires a corresponding evaluation device which makes the devices much more expensive. Electronic systems are also complex, prone to failure and manipulable. Simple safety measures are therefore required.

A further problem arises when removing and disposing of needle modules. Unlike unused needle modules, the needle is not covered by any cap and/or packaging after use so there is a risk of injury. The operator can easily prick himself and other people can also easily be injured.

It has surprisingly now been found that a needle module can overcome existing problems with the aid of a mechanical safety device which irreversibly blocks a driving out of the needle from the needle module during and after the removal of the needle module from the drive unit.

The invention therefore solves the above objects by means of a needle module comprising a piercing means on a mounting, which can be releasably coupled to a drive unit so that, as a result of a driving force exerted by the drive unit on the mounting, a repeated pushing movement moving the piercing means in and out is transmitted, wherein the mounting has a safety device which mechanically irreversibly blocks the piercing means after the needle module has been released from the drive unit so that it can no longer be moved out of the needle module.

The invention also relates to a device, in particular a hand device, for piercing the skin, comprising a drive unit and the needle module, wherein the drive unit has a motor and coupling means, and the needle module comprises a piercing means on a mounting, which can be releasably coupled to a drive unit so that, as a result of a driving force exerted by the drive unit on the mounting, a repeated pushing movement moving the piercing means in and out is transmitted, wherein the mounting has a safety device which mechanically irreversibly blocks the piercing means after the needle module has been released from the drive unit so that it can no longer be moved out of the needle module.

The needle module and device according to the invention therefore guarantee that a needle module cannot accidentally be used more than once. Such multiple use runs the risk of cross-contamination where pathogens are transferred from one treated person to the next.

A major advantage of the invention is that the risk of injury when removing and disposing of the needle module is greatly reduced. The risk of one accidentally pricking oneself or of other people nearby being pricked with a dirty needle lying freely exposed is virtually ruled out.

The needle module according to the invention has, as piercing means, a needle or a needle system with two, three or even more needles. The needles are designed in a manner known per se. It is expedient if the piercing means is covered, before use, with a protective cap which is only removed after the needle module has been coupled to the drive unit. A protective cap is particularly preferred if the piercing means projects from the needle module before use. It is also preferred if the needle module is sterilized and/or stored in a packaging until use.

The needle module also has a mounting for the piercing means, which can be re-releasably coupled to the drive unit. The repeated pushing movements generated by the drive unit are transmitted to the piercing means via the mounting. As a result, the piercing means is repeatedly moved out of the needle module to pierce the skin and then back into it.

The coupling may have different structural characteristics. The drive unit has a coupling means, e.g. preferably a push rod. For coupling purposes, corresponding parts of releasable connection means are formed as coupling elements on the coupling means and mounting. For example, the mounting or the coupling means may have a ball at the end which can be positively connected to a socket on the coupling means or the mounting. Furthermore, a ferromagnetic metal may also be integrated in the mounting (in the coupling means), which is attracted by a magnet in the drive unit (in the mounting) so as to produce a force fit. Further possible types of coupling are, in particular, the use of Velcro tapes and other adhesive tapes. The re-releasable connection is maintained during the piercing through a dynamic, oscillating back-and-forth movement of the push rod of defined amplitude and is to be dimensioned according to the existing dynamic forces.

The needle or needles are fixed to the mounting in a manner known per se.

The needle module also comprises an external cover, for example an enclosed housing. In a preferred embodiment, the housing is designed in two parts and comprises a top module at the tip, in which essentially the piercing means is located, and a base module in which essentially the mounting is arranged. Because it is divided into two parts, the housing can be manufactured cheaply by means of injection moulding.

According to the invention, provision is preferably made for the cover to overlap a housing of the drive unit so that the area in which the mounting is coupled to the drive unit is shielded from the outside not only during operation but also on coupling.

Expediently, a guide of the piercing means or of the mounting is formed. The guide can be formed integrally with the cover, or preferably as a separate part which is fixed to the cover. It is particularly preferred if the guide surrounds the mounting in the form of a ring. Expediently, the guide is established with a bulge on the outer circumference in a groove on the cover. However, a guide may also be produced in some other way.

The safety device provided according to the invention becomes active when the coupling of the needle module and drive unit is released in that a mechanical blockade of the piercing means is produced. After the safety device has been activated, it is no longer possible to move the piercing means out of the needle module. As a result, any re-use and risk of injury is excluded.

The safety device consists, for example, of a projection and a safety element. One part of these two is positioned on the mounting and the other part is positioned on the cover of the needle module, these parts being positioned in relation to one another so that the safety element, before and during use, lies in all positions of the piercing means in front of the projection as viewed from the side of the piercing means, and, on withdrawal of the needle module, is moved behind the projection.

The safety element is formed entirely or partially of an elastic material. The dimensions of the projection and safety element are determined so that the safety element cannot be moved past the projection without the exertion of force. The force which is required when removing the needle module from the drive unit in order to move the safety element behind the projection is smaller here than the adhesive force of the coupling. While the safety element is being moved past the projection, an elastic deformation takes place so that it can be moved past the projection. As soon as it has passed the projection, it reforms and can then no longer move back past the projection to the starting position without the exertion of force.

The three-dimensional arrangement of the projection and safety element is preferably chosen so that the exertion of force in order to move past the projection is less than any exertion of force required to move back. This can be achieved, for example, by using, as a safety element, springs or flexible tongues which can easily be pressed in one direction but spread apart in the opposite direction and de facto rule out any retraction. Preferably, the exertion of force in order to move the safety element out of the use position behind the projection is low.

In a first preferred embodiment, the elastic safety element is a spring, flexible tongue or barb. The projection may, for example, be a bulge or collar and it is preferably formed by the guide. However, it is also possible to structure the projection and guide as separate parts.

In a preferred embodiment, the safety element is formed by a barb or a flexible tongue, or a number of them, on the mounting and the projection is formed by the guide.

In a second preferred embodiment, a ring of flexible tongues is provided on the cover, preferably on the guide, of the needle module as a safety element and the projection is a bulge, collar or O-ring on the mounting.

In an alternative embodiment of the safety device, the mechanical blockade is carried out by the piercing means being withdrawn from its outlet opening in the cover of the needle module on decoupling from the drive unit and the mounting having a radial play. As soon as the piercing means is no longer centred in the outlet opening, it can no longer be brought back into it because the mounting has insufficient centring to hit the opening or is even pressed out of this centred position by mean of an elastic element or a non-centred bearing. It is preferred here if the cover of the needle module makes it more difficult to hit the opening in that the latter is located at the tip of a cone pointing with its tip towards the drive unit.

Further preferred in this embodiment is the fact that the cover of the needle module and the drive unit protect the area of the coupling elements from access so that the mounting cannot be centred manually. Expediently, a sufficient overlap of the housing is therefore provided.

Other embodiments of the safety device are conceivable, the only important thing being that, as a result of decoupling the needle module from the drive unit, a mechanical blockade of the piercing means is produced which fixes the latter irreversibly inside the needle module.

In a preferred embodiment, the needle module comprises a locking mechanism. The locking mechanism may, for example, be made of plastic and/or metal. Before use, the piercing means is fixed by the locking mechanism. When the needle module is coupled to the drive unit, the locking mechanism is released so that the fixing of the piercing means is removed. For example, the locking mechanism may be a pin, bolt or web which engages in a recess on the mounting of the piercing means or is secured to the mounting. To release it, the pin/bolt is taken out or the web removed, e.g. broken off or detached. As a result, the mounting coupled to the drive unit can be moved freely by the latter as intended and insert the piercing means into the skin and take it out again. The locking mechanism facilitates the fitting of the needle module onto the drive unit.

In a preferred embodiment, the locking mechanism is integrated into the guide in that the guide has at one point an aperture through which a pin/bolt engages in a recess on the mounting. As a result of this construction, a particularly simple structure of the needle module can be achieved which is also advantageous irrespective of the safety factor. The invention therefore also relates to a needle module in which the mounting is mounted with a guide and the guide has a locking mechanism for fixing the piercing means until use.

The drive unit comprises a coupling means, preferably a push rod, for transmitting the pushing movement to the mounting in the needle module. A gear unit is usually provided. The drive unit typically also forms the grip by which the device for piercing the skin is held.

The device also comprises a power supply. Usually provided in the drive unit is a drive, in particular an electric motor, which generates the repeated pushing movement. The drive unit is supplied with electricity here through a mains cable, if necessary via a mains adapter, or operated by an accumulator or a battery.

An on/off switch and control devices for the repetition speed and/or the insertion depth are typically provided. Switches and controls can be accommodated in the drive unit or in a control device. If a control device is provided, any necessary mains adapter is preferably integrated into it. The on/off switch is preferably located on the drive unit. For safety reasons, it may be designed as a pressure switch so that the pushing movement is only provided or is only transmitted to the piercing means as long as the operator is holding down the switch.

The needle module and drive unit can be secured in a manner known per se against the use of unsuitable combinations of the two unless the specific coupling already prevents the use of a needle module which is not intended for the drive unit.

In one embodiment, in particular on use in the area of medicine, a reservoir for a substance to be applied into the skin can be integrated in the needle module. This is advantageous, for example, for vaccinations. However, it may also be advantageous, for the purposes of applying permanent make-up, for a normally required quantity of pigment to be provided in a reservoir in the needle module.

The invention is to be explained in more detail by reference to the enclosed figures, although it is not to be limited to the embodiments specifically described. The invention also relates to all combinations of preferred embodiments unless they are mutually exclusive. The terms "about" or "approx." in connection with a number mean that values at least 10% above or below or values 5% above or below and, in any case, values 1% above or below are included.

The figures here show the following:

FIG. 1 schematically shows the structure of a hand device with fitted needle module FIG. 2 shows a detail of the coupling (magnet and ferromagnetic metal)

Figure 6:
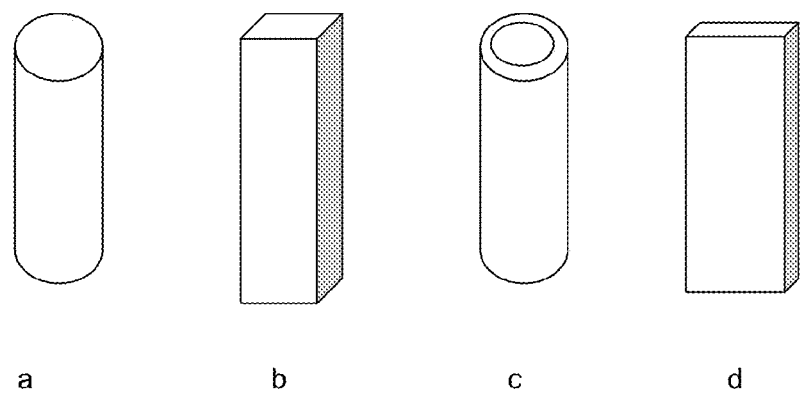

FIGS. 6 *a* to *d* show various embodiments of locking mechanisms

Figure 7:
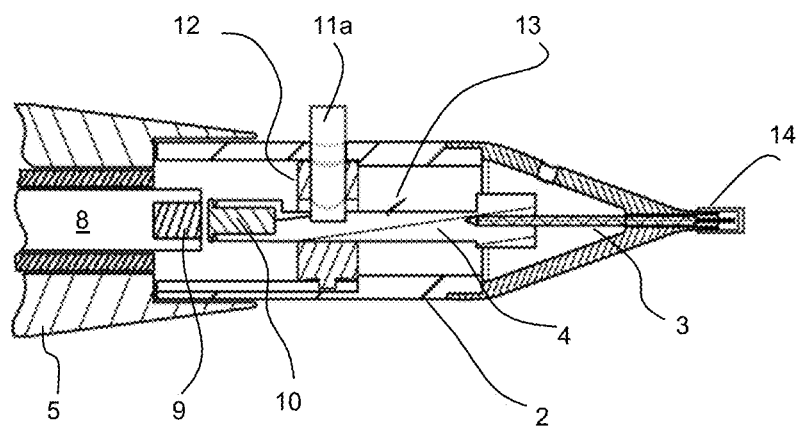
Figure 7:
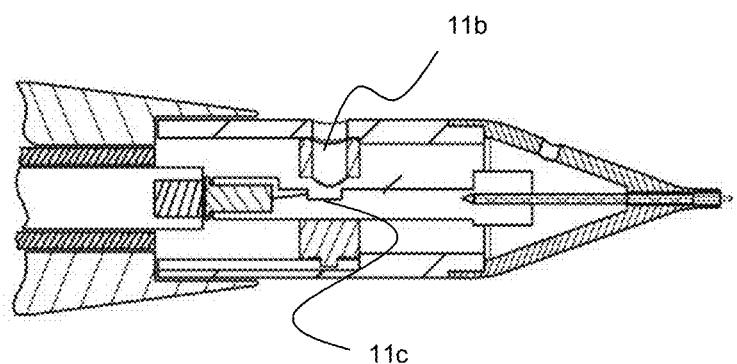
Figure 7:
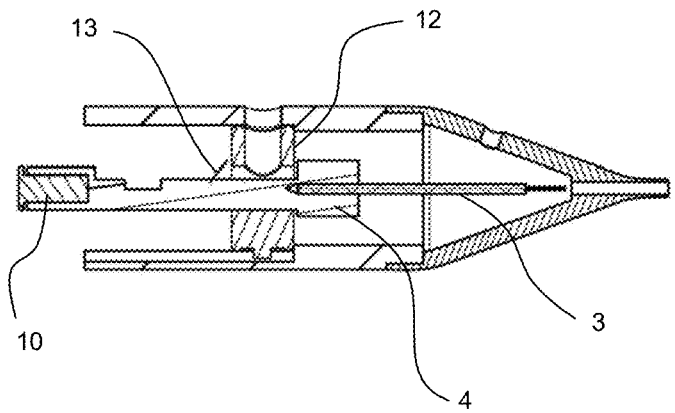
Figure 8:
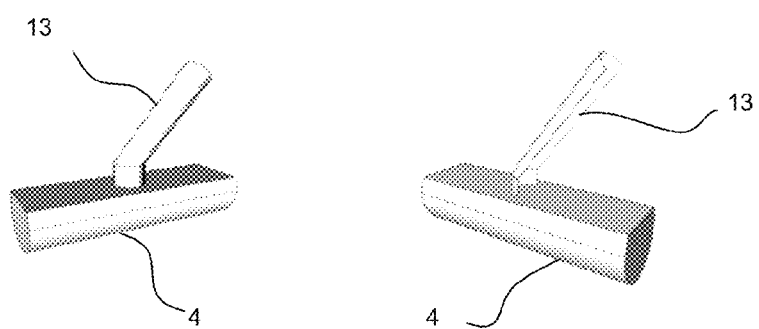

FIGS. 7 *a* to *c* show the hand device before use, the changes for use and the needle module after use FIG. 8 shows a safety element in detail.

Figure 1:
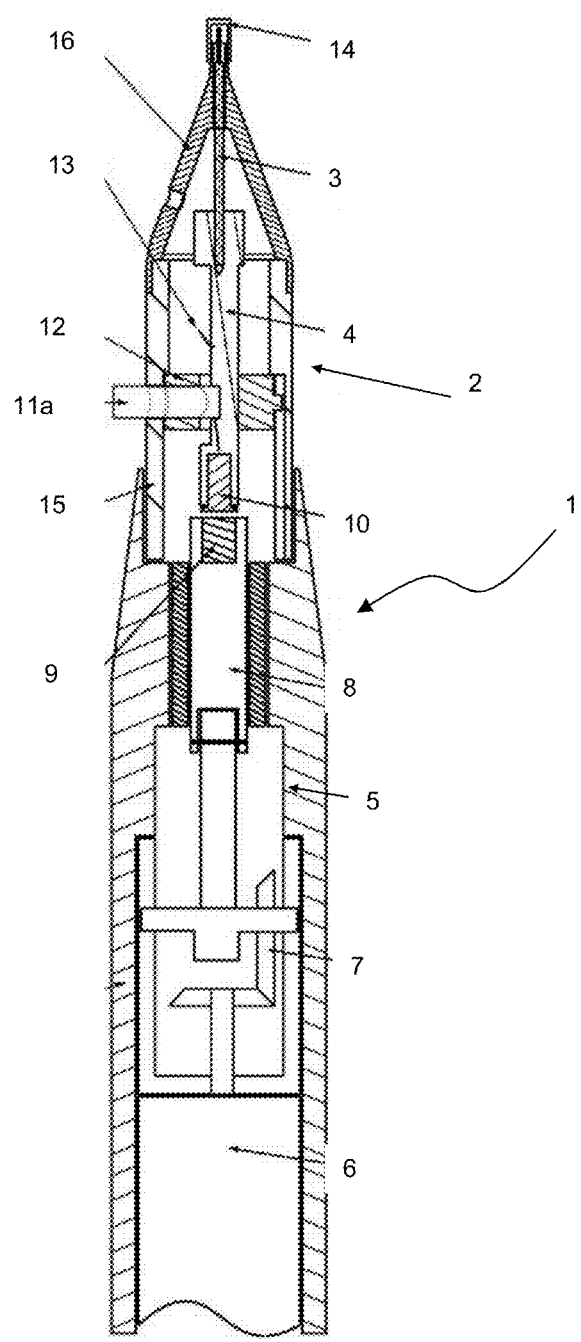

FIG. 1 schematically shows the structure of a hand device 1. The needle module 2 comprises a needle as piercing means 3 which is accommodated in a mounting 4. The drive unit 5 comprises a motor 6 which can be releasably coupled to the mounting 4 via a gear unit 7 and a coupling means 8 in the form of a push rod. The coupling of the mounting 4 to the drive unit 5 is carried out through a magnet 9 in the push rod 8 and a ferromagnetic material 10 in the mounting 4.

The needle module 2 also has a guide 12 which is simultaneously part of a locking mechanism 11 in that the guide 12 has an aperture 11*a* in which a bolt 11*b* is arranged which can engage in a recess 11*c* on the mounting 4. The mounting 4 is fixed until use with the aid of the bolt 11*a*. In the embodiment shown, the coupling is also only finally carried out when the bolt 11*a* is removed from the recess 11*c*. Only then can the mounting 4 come into direct contact with the push rod 8.

The safety device consists of a projection, which is formed by the guide 12, and the safety element 13. The needle 3 is covered by the protective cap 14 until use. It can also be seen that the needle module 2, in this case, has a cover which is designed in two parts and consists of a base module 15 and a top module 16.

The needle 3 is usually connected firmly and unreleasably to the mounting 4. At the start of treatment, the operator chooses a needle module 2 with the desired needle geometry and diameter. A number of needle modules 2 with different needles 3 are usually used during treatment.

Figure 2:
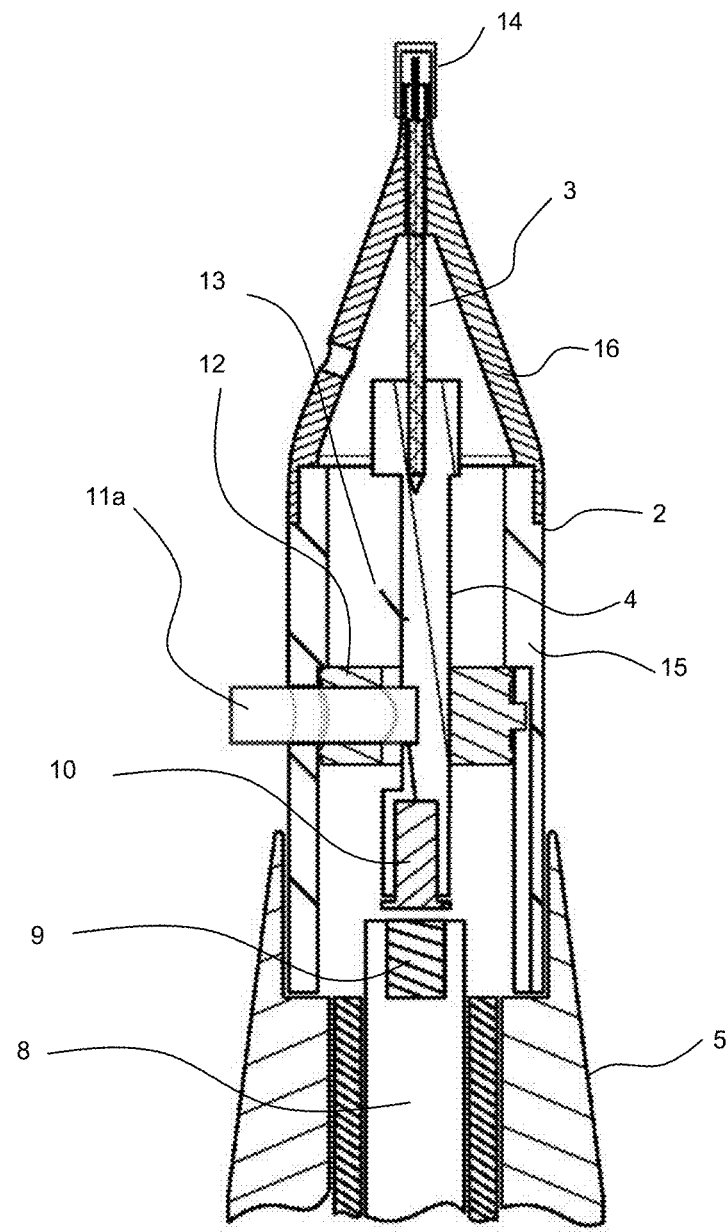

FIG. 2 shows the needle module 2 coupled to the drive unit 5 again in enlarged form. The mounting 4 contains a coupling element which allows a simple, re-releasable connection to the push rod 8 of the drive unit 5. Structural designs of the coupling element include, for example, positive snap-connection elements, clamping and adhesive connections, Velcro tapes or magnet elements.

Figure 3:
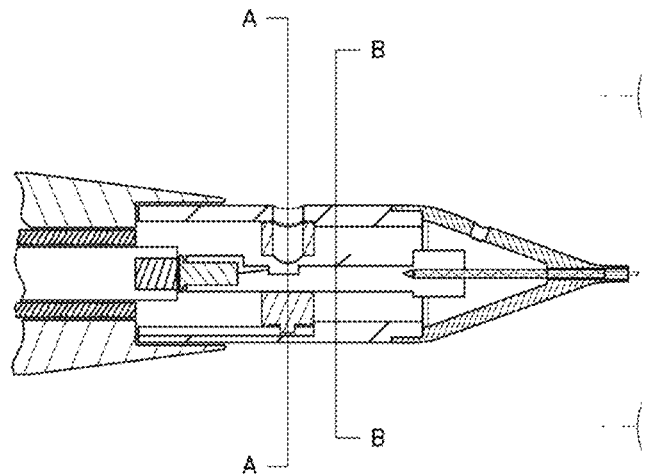
FIG. 3 shows cross sections of the needle module along the lines A-A and B-B
Figure 3:
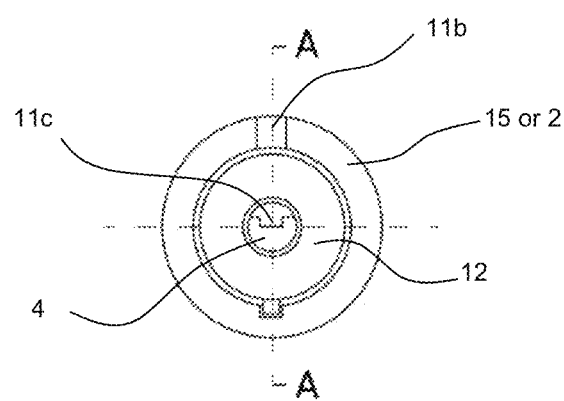
Figure 3:
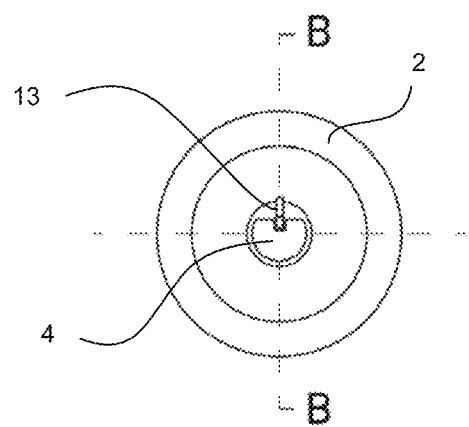

FIG. 3 at the top shows the needle module 2 once again, lines A-A and B-B being indicated. The two cross sections along these lines can be seen at the bottom of FIG. 3. It can be seen from the cross section along A-A that the guide 12 and the cover 15 of the needle module 2 have, as part of the locking mechanism 11, an aperture 11*b* through which the bolt 11*a* shown in FIG. 2 can engage in order then to engage in the recess 11*c* of the mounting 4 and hence fix the mounting 4.

It can also be seen from FIG. 3 that the mounting 4 is guided in the guide 12 which also forms the projection for the safety device. The mounting is flattened in the area between the coupling element 10 and the fixing of the piercing means 3. As can be seen from the section B-B, this facilitates the dimensioning of the safety element 13 and gives it space for its elastic deformation while it is being drawn past the guide 12 (which forms the projection). As an alternative to flattening, a groove, for example, could also be provided into which the safety element can deform.

Figure 4:
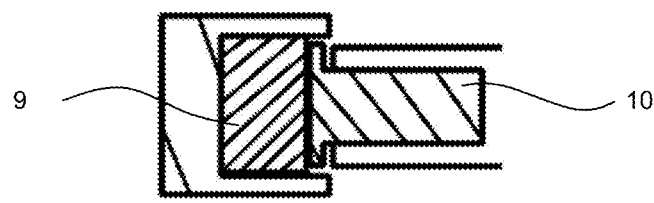
FIG. 4 shows alternative coupling variations
Figure 4:
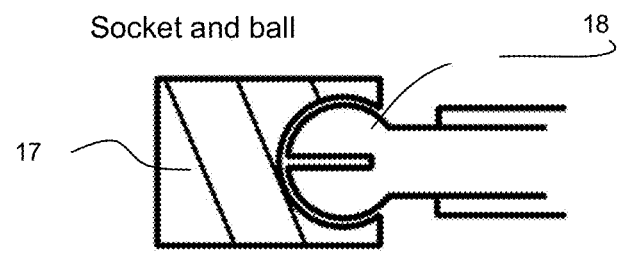
Figure 4:
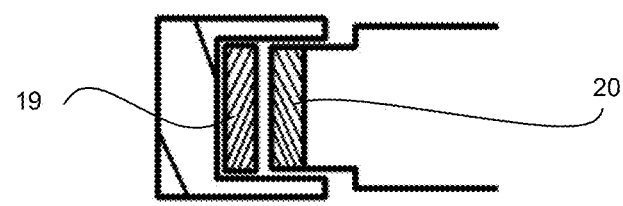

FIG. 4 shows various examples of coupling elements for the device 1 according to the invention. FIG. 4*a* again shows the magnetic coupling, wherein the magnet can of course also be located in the mounting and the magnetic material can be located on the push rod. FIG. 4*b* shows a coupling via socket 17 and ball 18. According to FIG. 4*c*, the corresponding hook component 19 and loop component 20 parts of a Velcro fastener are provided on the mounting and drive unit. These coupling means can of course also be arranged the other way round.

Figure 5:
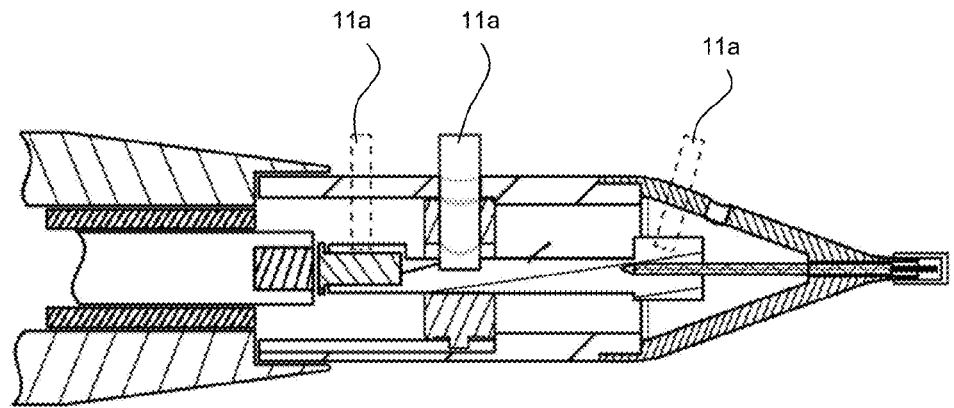
FIG. 5 shows various positions for a locking mechanism

FIG. 5 shows how any desired geometric location of the locking mechanism 11 in the direction of movement may be chosen. FIGS. 6*a* to *d* show schematic examples of embodiments of locking mechanisms 11. The mechanism 11 should have sufficient mechanical strength in terms of material and deformation (flexural rigidity) here so that while the needle module 2 is being fitted onto the drive unit 5 the mounting 4 remains in its initial position.

FIGS. 7*a* to c show the needle module 2 during and after treatment. After fitting of the needle module 2 and before the start of treatment, the locking mechanism 11 is released, i.e. the bolt 11 *a* is withdrawn, as shown in FIG. 7*a*. After this unblocking, the magnet 9 of the push rod 8 of the drive unit 5 attracts the mounting 4 with the magnetic material 10 and forms a force-fitted connection.

The mounting 4 is guided in what is referred to as a guide 12, wherein the locking mechanism 11 can be integrated into the guide 12 as shown. The guide 12 guarantees an essentially straight, guided back-and-forth movement of the mounting 4 with the needle 3. This prevents any bending or deviation of the needle 3 out of the direction of movement under load. The guide 12 may be arranged in any desired location along the axis of movement of the mounting 4. The guide 12 is ideally located centrally in the area of the mounting 4 because this, owing to its functions as a needle holder, has a sufficient mechanical flexural rigidity and strength.

In the embodiment shown, the guide 12 together with the safety element 13, according to the invention, also has the function of irreversibly restricting the movement of the needle 3 with the mounting 4 after the separation of the needle module 2 and drive unit 5. This takes place through a specifically chosen arrangement of the guide 12 and safety element 13. The safety element 13 is made, in particular, out of plastic or metal and may be designed in one or more parts, in particular as a fan element. FIG. 8 shows an example.

The safety element 13 is arranged in the direction of the axis of movement so that, firstly, it does not prevent the back-and-forth movement of the needle 3 after the needle module 2 has been coupled to the drive unit 5, i.e. during treatment, e.g. the insertion of dye. Secondly, after separation of the needle module 2 and drive unit 5, i.e. after treatment has come to an end, it enables the needle 3 to be inserted irreversibly and completely in needle module 2 and holds it securely there. The needle 3 can no longer be moved out of the needle module 2. FIG. 7c shows this state.

In particular, the safety element 13 moves through the guide 12 during the separation process described above. In doing so, it deforms so that a renewed movement of the needle 3 into the direction of the initial position is structurally prevented.

LIST OF REFERENCE NUMERALS

1 Device, in particular a hand device
2 Needle module
3 Piercing means, i.e. a needle or needle system
4 Mounting
5 Drive unit
6 Motor
7 Gear unit
8 Coupling means, in particular a push rod
9 Magnet coupling element
10 Magn. material coupling element
11 Locking mechanism with 11a bolt, 11b aperture and 11c recess
12 Guide, also a projection as part of the safety device
13 Safety element
14 Protective cap
15 Base module
16 Top module
17 Socket as coupling element
18 Ball as coupling element
19 Hook component as coupling element
20 Loop component as coupling element

The invention claimed is:

1. A needle module comprising a piercing element arranged on a mounting, which can be releasably coupled to a drive unit so that, as a result of a driving force exerted by the drive unit on the mounting, a repeated pushing movement moving the piercing element in and out is transmitted, wherein the mounting has a safety device which mechanically and irreversibly blocks the piercing element after the needle module has been released from the drive unit so that it can no longer be moved out of the needle module.

2. The needle module according to claim 1, wherein the piercing element has a needle or a needle system with two, three, or more than three needles.

3. The needle module according to claim 1, wherein the safety device comprises a safety element and a projection, wherein the safety element is made of an elastic material.

4. The needle module according to claim 3, wherein the projection is formed by a guide, wherein the safety element is in the form of a flexible tongue, or a barb, or a fan element, and wherein the safety element is positioned on the mounting so that when the needle module is withdrawn from the drive unit, the safety element is drawn past the projection and the projection blocks any backwards movement.

5. The needle module according to claim 3, wherein the safety element is a spring or a ring of flexible tongues or barbs on the cover of the needle module and the projection is a bulge, collar, or O-ring on the mounting so that, when the needle module is withdrawn from the drive unit, the safety element is drawn past the projection and the projection blocks any backwards movement.

6. The needle module according to claim 1, further comprising a locking mechanism which fixes the mounting in an initial position within the needle module until use.

7. The needle module according to claim 1, further comprising a guide which guarantees an essentially straight, guided back-and-forth movement of the mounting with the piercing element.

8. A device for piercing the skin, comprising a drive unit and a needle module, wherein the drive unit has a motor element and a coupling element, and the needle module comprises a piercing element on a mounting, which can be releasably coupled to the drive unit so that, as a result of a driving force exerted by the drive unit on the mounting, a repeated pushing movement moving the piercing element in and out of the needle module is transmitted, wherein the mounting has a safety device which mechanically and irreversibly blocks the piercing element after the needle module has been released from the drive unit so that it can no longer be moved out of the needle module.

9. The device according to claim 8, wherein the drive unit has a coupling element.

10. The device according to claim 9, further comprising corresponding parts of a releasable connection element formed on the coupling element and the mounting for the coupling of drive unit and needle module.

11. The device according to claim 10, wherein the corresponding parts of the releasable connection element are selected from the group consisting of a ball and a socket, a magnet and a ferromagnetic material, and hook and loop components.

12. A needle module comprising a piercing element on a mounting, which is releasably coupled to a drive unit so that, as a result of a driving force exerted by the drive unit on the mounting, a repeated pushing movement moving the piercing element in and out of the needle module is transmitted, wherein the mounting comprises a guide with an integrated locking mechanism, wherein the guide together with an outlet opening for the piercing element in a cover of the needle module guarantees an essentially straight, guided back-and-forth movement of the mounting with the piercing element and the locking mechanism fixes the mounting in an initial position within the needle module until use, wherein the piercing element projects from the needle module and is covered with a protective cap before use.

13. The needle module according to claim 12, wherein the mounting has a radial play and, when the needle module is released from the drive unit, the piercing element is drawn into the inside of the cover of the needle module so that it cannot move back out through the outlet opening owing to the radial play of the mounting.

14. The needle module according to claim 12, wherein the mounting, is forced out of a centered position after the needle module has been released from the drive unit due to an elastic element or a non-centered bearing so that the mounting cannot move back out through the outlet opening.

15. The needle module according to claim 12, wherein a cone with its tip pointing towards the drive unit is formed on the tip of the cover of the needle module.

16. The needle module according to claim 14, wherein the cover of the needle module consists of a base module and a top module.

17. The needle module according to claim 4, wherein the needle module has a locking mechanism which fixes the mounting in an initial position within the needle module until use.

18. The needle module according to claim 5, wherein the needle module has a locking mechanism which fixes the mounting in an initial position within the needle module until use.

19. The needle module according to claim 4, wherein the needle module comprises a guide which guarantees an essentially straight, guided back-and-forth movement of the mounting with the piercing element.

20. The needle module according to claim 5, wherein the needle module comprises a guide which guarantees an essentially straight, guided back-and-forth movement of the mounting with the piercing element.

21. The needle module according to claim 6, further comprising a guide which guarantees an essentially straight, guided back-and-forth movement of the mounting with the piercing element.

22. The needle module according to claim 14, wherein a cone with its tip pointing towards the drive unit is formed on the tip of the cover of the needle module.

23. The needle module according to claim 15, wherein the cover of the needle module consists of a base module and a top module.

24. The device according to claim 9, wherein the coupling element is a push rod.

25. The device according to claim 24, further comprising corresponding parts of a releasable connection element formed on the coupling element and the mounting for the coupling of drive unit and needle module.

26. The device according to claim 25, wherein the corresponding parts of the releasable connection element are selected from the group consisting of a ball and a socket, a magnet and a ferromagnetic material, and hook and loop components.

27. The device according to claim 8, wherein the device is a hand device.

28. The device according to claim 26, wherein the device is a hand device.

* * * * *